United States Patent [19]

Gubitosa et al.

[11] Patent Number: 5,496,786
[45] Date of Patent: Mar. 5, 1996

[54] CATALYST FOR REDUCING LOWER POLYHYDRIC ALCOHOLS BY HYDROGENOLYSISAL HIGHER POLYHYDRIC ALCOHOLS AND METHOD FOR PREPARING CATALYST

[75] Inventors: Giuseppe Gubitosa, Novara; Bruno Casale, Cameri, both of Italy

[73] Assignee: Novaol S.r.l., Italy

[21] Appl. No.: 319,455

[22] Filed: Oct. 6, 1994

Related U.S. Application Data

[62] Division of Ser. No. 9,127, Jan. 26, 1993, Pat. No. 5,354,914.

[30] Foreign Application Priority Data

Jan. 31, 1992 [IT] Italy ................... TO92A0081

[51] Int. Cl.$^6$ .......................... B01J 23/46
[52] U.S. Cl. .......................... 502/182; 502/185
[58] Field of Search .................. 502/182, 185

[56] References Cited

U.S. PATENT DOCUMENTS

| | | | |
|---|---|---|---|
| 3,055,840 | 9/1962 | Koch, Jr. .................. | 252/443 |
| 4,218,401 | 8/1980 | Wymore .................. | 567/402 |
| 4,430,253 | 2/1984 | Dubeck et al. ............ | 502/185 |
| 4,914,071 | 4/1990 | Collins et al. ............ | 502/185 |

*Primary Examiner*—E. Rollins Cross
*Assistant Examiner*—Timothy H. Meeks
*Attorney, Agent, or Firm*—Bryan Cave

[57] ABSTRACT

A metallic catalyst composition on an inert support, suitable in particular for hydrogenolysis reactions of higher polyhydric alcohols, which comprises the following relative to 100 parts of the catalyst:

a) 0.5 to 5 weight % ruthenium;

b) 1 to 10 weight % tin.

The catalyst is used in particular for producing lower polyhydric alcohols such as ethanediol, propylene glycol, butanediol and glycerol, by means of hydrogenolysis reaction of higher polyhydric alcohols.

4 Claims, No Drawings

CATALYST FOR REDUCING LOWER POLYHYDRIC ALCOHOLS BY HYDROGENOLYSISAL HIGHER POLYHYDRIC ALCOHOLS AND METHOD FOR PREPARING CATALYST

CROSS-REFERENCE TO RELATED APPLICATION

This is a divisional of U.S. application Ser. No. 08/009,127, filed Jan. 26, 1993, which issued as U.S. Pat. No. 5,354,914.

BACKGROUND OF THE INVENTION

The present invention relates to methods for hydrogenation of carbohydrates and hydrogenolysis of higher polyhydric alcohols, and to a new hydrogenation catalyst which is useful for producing lower polyhydric alcohols from renewable materials, such as in particular carbohydrates and higher polyhydric alcohols.

In the present description, the term "higher polyhydric alcohols" means products such as sorbitol, mannitol and xylitol derived from catalytic hydrogenation of carbohydrates (and in particular of glucose, fructose and their mixtures).

The term "lower polyhydric alcohols" means polyalcohols having a maximum of 6 carbon atoms and a maximum of 3 hydroxyl groups, in particular ethanediol, propylene glycol, butanediol and glycerol.

The invention also relates to a method for preparing the new catalyst.

DESCRIPTION OF THE PRIOR ART

U.S. Pat. No. 2,868,847 describes a method for catalytic hydrogenation of mono- and disaccharides for producing polyhydroxyl alcohols, in particular sorbitol, and proposes replacing the known platinum and palladium- based catalysts used for this method, by a ruthenium catalyst or by a metallic catalyst based on ruthenium and platinum or palladium.

U.S. Pat. No. 4,476,331 describes a method for producing lower polyhydric alcohols comprising a first stage of hydrogenation of carbohydrates to produce higher polyhydric alcohols and a second stage in which the higher polyhydric alcohols are subjected to hydrogenolysis in the presence of a ruthenium-based catalyst which is presulphonated or is sulphonated in use by addition of sulphonated compounds to the reactive medium. Sulphonation of the ruthenium-based catalyst is necessary in order to limit the hydrogenolysis reaction which would otherwise lead to the formation of highly hydrogenated compounds such as hydrocarbons, and in particular methane.

SUMMARY OF THE INVENTION

The main object of the present invention is to provide a method for hydrogenolysis of higher polyhydric alcohols which has a high level of selectiveness towards the production of lower polyhydric alcohols, thus keeping to a minimum the formation of gaseous hydrocarbons which constitute an undesirable product.

To that end, a first object of the present invention is a new metallic catalyst on an inert support, comprising the following relative to the (anhydrous) weight of the catalyst:

a) 0.5 to 5 weight % ruthenium;

b) 0.1 to 10 weight % tin.

A second object of the invention is a method for producing lower polyhydric alcohols and their mixtures by means of hydrogenolysis under pressure of higher polyhydric alcohols, using the catalyst previously described.

DESCRIPTION OF THE PREFERRED EMBODIMENTS

The catalyst support preferably comprises powdered or granulated activated carbon. For continuous fixed bed hydrogenation and hydrogenolysis methods, a granulated activated carbon is preferably used, which has:

a specific surface area of 600 to 1000 $m^2/g$ and preferably 800 to 1000 $m^2/g$ (B.E.T. method);

a total pore volume of 0.5 to 1.2 $cm^3/g$ and preferably 0.6 to 0.7 $cm^3/g$ (combined nitrogenmercury method);

an apparent specific weight (bulk density) of 0.3 to 0.8 $gr/cm^3$ and preferably 0.45 to 0.55 $g/cm^3$;

an actual specific weight of 1.9 to 2.3 $g/cm^3$;

a total volume of micropores having a radius smaller than 75 A of 0.4 to 0.55 $cm^3/g$; and an ash content of 2 to 5 weight %

As used herein, granulated activated carbon means a carbon in which the minimum granule size is at least 0.5 mm and which has a particle size of between 5.7 and 0.5 mm (3–32 mesh; Tiller series). The optimum particle size is selected on the basis of the process parameters, according to known criteria.

Granulated activated carbon of the above-described type is available commercially from ACQUE NYMCO under references GH-12132 and CA-12132.

In the hydrogenolysis reaction of higher polyhydric alcohols, the catalyst preferably has:

a') 1.5 to 3 weight % ruthenium; and b') 1 to 3 weight % tin.

The atomic ratio between ruthenium and tin is preferably of from 2 to 1.

According to the invention, the catalyst supported on activated carbon is prepared by a method which comprises the following operations.

An aqueous solution is prepared which contains a compound of ruthenium and tin, such that after the support has been impregnated, a concentration within the limits previously indicated of metal in the catalyst is obtained. The precursor used for the active elements is a ruthenium compound soluble in water, and preferably ruthenium trichloride, and a soluble compound of tin, and preferably $SnCl_2 \cdot 2H_2O$.

The aqueous solution containing the metals is then put into contact with an aqueous solution of the activated carbon, followed by adjustment of the pH by addition of an alkaline agent until a value of 4.5 to 8 is obtained. In a preferred embodiment, the activated carbon is in the granulated form previously described. The aqueous solution of catalytic compounds is put into contact with the suspension containing the support, and the pH of the suspension thus obtained is preferably allowed to stabilise at a value of approximately 1. An aqueous solution of an alkaline compound is then added in a quantity such that the pH of the resulting suspension is between 4.5 and 5. After approximately an hour the pH is regulated by means of further addition of the alkaline agent to a value no higher than 8 and preferably to between 6 and 8.

The suspension is then heated a temperature of between 70° and 100° C., and is maintained at this temperature for a length of time which is generally between 30 minutes and 2 hours, and is sufficient to give rise to depositing of compounds of the metals on the activated carbon, which is then separated from the suspension. During this impregnation process the two metals are deposited on the support substantially in the form of highly dispersed oxides in close contact with one another, in concentrations of 0.5 to 5 weight % ruthenium and 0.1 to 10 weight % tin.

The separated solid thus obtained is then suspended in an alkaline solution, and the suspension thus obtained is processed with gaseous hydrogen at a temperature of between 60° and 100° C. for 1 to 4 hours and preferably for two hours.

The alkaline agent used in order to regulate the pH and to suspend the catalyst for the treatment with hydrogen may be a hydroxide, a carbonate or a bicarbonate of the alkaline elements, and preferably sodium carbonate.

The catalyst thus obtained maintains the characteristics of porosity, specific surface area and specific weight particular to the original activated carbon.

The method for hydrogenolysis of higher polyhydric alcohols according to the invention is preferably carried out continuously on a fixed bed reactor. The reaction temperature is generally between 200° and 300° C. and preferably 220°–270° C., the spatial velocity of the fluid is between 0.3 and 4 $h^{-1}$ and preferably between 0.6 and 2.50 $h^{-1}$, and the reaction pressure is between 5 and 20 MPa and preferably between 7.5 and 15 MPa. The continuous reactor is preferably supplied with a reaction promoter selected from amongst alkaline and alkaline-earth hydroxides, and preferably sodium hydroxide or calcium hydroxide, or basic reaction salts; the molar ratio between higher polyhydric alcohols and the promoter supplied is between 2 and 30.

In the hydrogenolysis method, the supply comprises a higher polyhydric alcohol or mixture of polyhydric alcohols, supplied to the hydrogenation reactor preferably in an aqueous solution having a concentration of 20 to 40 weight %.

The higher polyhydric alcohol or mixture of higher polyhydric alcohols is advantageously obtained in a first stage of hydrogenation of carbohydrates carried out with a low basic pH, preferably of between 7.5 and 8, at a reaction temperature of between 120° and 150° C. This first stage is also preferably carried out in an aqueous solution, in the presence of a basic promoter such as those previously described, in a quantity sufficient to maintain the pH in the aforementioned field. The reaction is preferably carried out on a fixed bed, using a catalyst comprising 0.5 to 5 weight % ruthenium supported on granulated activated carbon having the above-described characteristics. The preparation of this catalyst is similar to that described for the catalyst comprising ruthenium and tin, the only difference being that the tin compound is not used. In this first stage the carbohydrate may comprise monosaccharides or disaccharides. The preferred supply however comprises an aqueous solution of glucose, which is converted with virtually maximum theoretical yield into sorbitol. Sorbitol constitutes the preferred supply substrate for the hydrogenolysis process which, owing to use of the catalyst according to the invention, enables ethanediol, 1.2-propylene glycol, butanediol and smaller amounts of glycerol, lactic acid and monovalent alcohols, as well as any products such as erythritol and pentanediols to be obtained with a high level of selectiveness.

In this method the catalyst according to the invention enables the formation of undesirable gaseous hydrocarbons to be reduced without using sulphurated compounds either in the catalyst or in the reactive medium.

EXAMPLE 1

Preparation of the Catalyst

In preparing the catalyst according to the present invention, an activated carbon of vegetable origin and preferably derived from coconut (palm) having the following features is used:

specific surface area: 800 $m^2/g$;

actual specific weight: 2.1 $g/cm^3$;

total pore volume: 0.64 $cm^3/g$;

volume of micropores (R<75 A): 0.5 $cm^3/g$;

apparent specific weight (bulk density) 0.48 $g/cm^3$;

ash content: 3 weight;

particle size:
  10–18 mesh: (Tiller series 2÷1 mm): 20–30 weight %
  18–35 mesh: (Tiller series 1÷0.5 mm): 80–70 weight %

A quantity of 112.5 g granulated activated carbon of this type having 8% humidity is suspended in 300 $cm^3$ of distilled water, and is subjected to continuous mechanical agitation. After approximately 30 minutes the pH of the suspension is 10.2.

150 ml solution of $RuCl_3$ and $SnCl_2$ containing 3.87 g Ru and 2.24 g Sn acidified by hydrochloric acid is added slowly to this suspension. The pH of the suspension 40 minutes after this addition is completed is 1.3; it is then increased to 4.8 by adding a 1M solution of sodium carbonate, and after approximately 60 minutes the pH is increased to 6 by means of a further addition of sodium carbonate. The suspension is then heated to a temperature of 90° C. and is maintained at this temperature for approximately 1 hour.

The solid is separated from the suspension by means of filtering and washing. It is then re-suspended in 2 liters of 0.1M solution of sodium carbonate. An argon flow is bubbled through the suspension, which is contained in a three-necked flask while being gently agitated mechanically, until the air is entirely removed. The argon flow is then replaced by a hydrogen flow and the suspension is reheated to a temperature of 80° C. The suspension is maintained at 80° C. for approximately 2 hours. The hydrogen flow is then replaced by an argon flow, and the suspension is cooled to 60° C. The catalyst is filtered and washed until there are no chlorides left in the washing waters. The catalyst which has a ruthenium and tin base is kept in a sealed container, and has the concentrations in weight of the activated metals listed in Table 1 (catalyst A).

The above procedure is repeated varying the quantity of ruthenium and tin such as to obtain catalysts with different atomic ratios of ruthenium/tin (catalysts B and C in Table 1).

TABLE 1

| Catalyst | Weight % humidity | Weight % Ru on dry product | Weight % Sn on dry product | Ru/Sn atomic ratio |
| --- | --- | --- | --- | --- |
| A | 40 | 2.3 | 1.35 | 2.0 |
| B | 42 | 2.3 | 2 | 1.3 |
| C | 38 | 1.9 | 2.2 | 1.0 |

EXAMPLES 2–6

Production of Lower Polyhydric Alcohols

The catalysts prepared according to example 1 are used for the conversion of sorbitol to lower polyhydric alcohols under various experimental conditions and using the following general method.

250 $cm^3$ of aqueous solution containing 80 g sorbitol, 5.4 g calcium hydroxide and a variable amount of catalyst is introduced into an autoclave which has a volume of 500 $cm^3$, and is provided with a manometer, a mechanical, magnetically driven agitator with four inclined blades, wash-plates, and a heating system. The autoclave is closed and the air it contains is eliminated by washing with inert gas. The inert gas is then replaced by hydrogen, and the autoclave is loaded under pressure to 13 MPa using hydrogen at ambient temperature. The heating and the agitation at 660 rpm are then begun, and the required temperature is reached after approximately 1 hour. This temperature is maintained for 2 hours. The pressure is increased to 15–19 MPa during the course of heating, and is then decreased to 12–16.5 MPa. After the two-hour period the autoclave is cooled down by recirculating water until ambient temperature is reached, and before the autoclave is de-pressurised a gas sample is collected for analysis. The reaction fluid is separated from the catalyst by filtration.

The gas sample collected is analysed by gas chromatography in order to ascertain the presence of any hydrocarbons (methane, ethane, ethylene, etc) and carbon dioxide. The reaction fluid is analysed by means of high pressure liquid chromatography (HPLC).

The fluid product contains mainly 1,2-propylene glycol, ethanediol, glycerol, lactic acid and a smaller amount of butanediols and monovalent alcohols. The gas contains small amounts of methane and traces of carbon dioxide.

The results of examples 2–6 are contained in tables 2 and 3 hereinafter.

Table 2 shows the catalysts used which have different atomic ratios of Ru/Sn (A,B,C), the quantity of catalyst used expressed by the sorbitol/ruthenium molar ratio, the reaction temperature, the initial $H^2$ pressure at ambient temperature and the conversion expressed as a ratio of sorbitol converted/sorbitol loaded. Table 3 shows the selectiveness towards the various reaction products.

It can be seen from table 2 that provided the remaining operative conditions are the same, the Ru/Sn atomic ratio affects the conversion, which increases from 80% (Ru/Sn=1:1) to 90% (Ru/Sn=1:0.5) Examples 2–4, whereas the formation of methane (table 3) increases as the Ru/Sn atomic ratio decreases, even though it remains at substantially low levels.

Conversion improvements are obtained without substantially altering the selectiveness, by increasing both the reaction temperature (example 6) and the quantity of catalyst in the reactive medium (example 5).

TABLE 2

| Example | Temp. (°C.) | Atomic ratio Ru/Sn | Molar ratio Sorbitol/ Ruthenium | Conversion (% sorbitol) |
|---|---|---|---|---|
| 2 | 250 | 1:1 | 340 | 80 |
| 3 | 250 | 1:0.75 | 340 | 86.3 |
| 4 | 250 | 1:0.5 | 340 | 89.3 |
| 5 | 250 | 1:1 | 160 | 86.0 |
| 6 | 270 | 1:1 | 340 | 87.7 |

EXAMPLES 7–10

The catalyst B prepared on a larger scale according to example 1, is loaded (100 cm$^3$) in a tubular fixed bed reactor which has a descending and equally distributed flow, equipped with a gas—fluid separator at the reactor outlet, a reaction fluid supply tank and a hydrogen gas tank. The reactor has a diameter of 20.5 mm (the height of the catalytic bed is 30 cm) and is equipped with a coaxial thermocouple which has 5 temperature measurement areas, disposed at 2.5, 8.5, 15, 21.5 and 28 cm below the topmost level of the catalytic bed. Above the catalytic bed there is a layer of inert material 7.5 cm deep, which ensures that the reagents are satisfactorily mixed before coming into contact with the catalytic bed itself.

The reactor is closed and is connected to a system which allows for the supply of the reagents and discharge of the products. The system is pressurised with nitrogen in order to check its airtightness. The reactor is then supplied at the test pressure with 2 flows: a mixed hydrogen—water flow obtained by injecting water into the hydrogen current, and a second flow of deionised water at ambient temperature. Before the two flows reach the catalytic bed they are thoroughly mixed through the layer of inert material. The reactor is then heated until it reaches the test temperature. In these conditions the water flow is replaced by a flow of aqueous sorbitol solution containing sodium hydroxide. After approximately 8 hours the system temperature and spatial velocity (LHSV) are in a steady state. After this stabilisation period collection of the chemical reaction products at two-hourly intervals begins. The fluid samples of the reaction products are analysed by means of high pressure liquid chromatography (HPLC). The gas output from the gas—fluid separator is measured and analysed by means of gas chromatography in order to ascertain the presence of any hydrocarbons (methane, ethane etc) and carbon dioxide. The fluid product contains mainly 1,2-propylene glycol, ethanediol, butanediol and a smaller amount of glycerol, lactic acid and monovalent alcohols, as well as products such as erythritol and pentanediol. The gas output from the reactor contains hydrogen and traces of carbon dioxide. The results of examples 12–14 for two different reaction temperatures and two different LHSV values are contained in tables 4 and 5 hereinafter, relative to the operative conditions and distribution of the reaction products.

The results given in table 5 show that by using this catalyst, the formation of methane and more generally of gaseous products is limited to very low values (0.3÷0.6%) irrespective of the temperature and LHVS values.

Furthermore if these results are compared with those obtained in the batch system using the same catalyst, it can be seen that in a continuous reaction system, the catalytic performance of the catalyst is improved.

TABLE 3

| | Distribution of the products (% of carbon atoms) | | | | | |
|---|---|---|---|---|---|---|
| Example | Methane | Ethanediol | 1-2 propylene glycol | Butanediol | Glycerol | Lactic acid |
| 2 | 1.6 | 20.5 | 38.8 | 9 | 5.3 | 6 |
| 3 | 1.6 | 21.4 | 40.5 | 8.5 | 5.2 | 5.3 |
| 4 | 1.6 | 21.5 | 39.4 | 8.0 | 8.0 | 3.8 |
| 5 | 2.0 | 18.9 | 38.5 | 9.8 | 5.3 | 4.0 |
| 6 | 2.1 | 20.2 | 38.4 | 9.6 | 4.4 | 4.8 |

The conversion increases substantially if the temperature is increased slightly, whereas the distribution of the products does not vary substantially.

TABLE 4

| Example | Total pressure (MPa) | Temp. (°C.) | S = supply (ppm) | Sorbitol/NaOH (molar ratio) | H2/Sorb. (molar ratio) | LHSV (h-1) | Conversion (% sorbitol) |
|---|---|---|---|---|---|---|---|
| 7 | 10 | 225 | 0 | 4 | 6 | 1.67 | 90.4 |
| 8 | 10 | 225 | 0 | 4 | 6 | 1.25 | 90.0 |
| 9 | 10 | 244 | 0 | 4 | 6 | 1.25 | 96.0 |
| 10 | 10 | 244 | 0 | 4 | 6 | 1.67 | 93.8 |

TABLE 5

| | Distribution of the products (% of carbon atoms) | | | | |
|---|---|---|---|---|---|
| Example | Methane | Ethane-diol | 1-2 propylene glycol | Butane-diol | Glycerol |
| 7 | 0.3 | 16.9 | 41.6 | 12 | 4.7 |
| 8 | 0.3 | 17.0 | 44.0 | 14 | 5.5 |
| 9 | 0.6 | 16.5 | 42.3 | 13 | 4.6 |
| 10 | 0.4 | 17.6 | 43.0 | 15 | 4.3 |

We claim:

1. A catalyst composition for hydrogenolysis reactions of higher polyhydric alcohols comprising:

0.5 to 5% by weight of ruthenium and 0.1 to 10% by weight of tin supported on granular carbon with an atomic Ru/Sn ratio of 1:1 to 2:1, said catalyst having:

a specific surface area of 600 to 1000 m$^2$/g;

a total pore volume of 0.5 to 1.2 cm$^3$/g;

a total volume of micropores having a radius smaller than 75 Å of 0.4 to 0.55 cm$^3$/g.

2. A catalyst composition according to claim 1, comprising:

a') 1.5 to 3 weight % ruthenium;

b') 1 to 3 weight % tin.

3. A method for preparing a catalyst composition for hydrogenolysis reactions of higher polyhydric alcohols, comprising the steps of:

I) preparing an aqueous solution consisting of a compound of ruthenium and tin;

II) putting this aqueous solution into contact with an aqueous suspension of activated carbon, and regulating the pH by adding an alkaline agent until a value of between 4.5 and 8 is obtained, the activated carbon having:

a) a specific surface area of 600 to 1000 m$^3$/g;

b) a total pore volume of 0.5 to 1.2 cm$^2$/g;

c) an apparent specific weight (bulk density) of 0.45 to 0.55 g/cm$^3$;

d) an actual specific weight of 1.9 to 2.3 g/cm$^3$;

e) a total volume of micropores having a radius smaller than 75 Å of 0.4 to 0.55 cm$^3$/g; and f) an ash content of 2 to 5 weight %;

III) heating to a temperature of 60° to 100° C. for a time sufficient to give rise to depositing of the metals on the activated carbon, and separating this solid;

IV) suspending the solid thus obtained in an alkaline solution and hydrogenating the suspension thus obtained with gaseous hydrogen at a temperature of between 60° and 100° C. for a time sufficient to give rise to reduction of the metals deposited on the support, the concentration of the metals in the solution I) being such as to obtain a catalyst composition comprising:

a) 0.5 to 5 weight % ruthenium;

b) 0.1 to 10 weight % tin.

4. A method according to claim 3, in which the aqueous solution in I) is prepared by dissolving in water RuCl$_3$ and SnCl$_2$ . 2H$_2$O.

* * * * *

UNITED STATES PATENT AND TRADEMARK OFFICE
CERTIFICATE OF CORRECTION

PATENT NO. : 5,496,786
DATED : March 5, 996
INVENTOR(S) : Gubitosa et al.

It is certified that error appears in the above-indentified patent and that said Letters Patent is hereby corrected as shown below:

| Column | Line | | |
|--------|------|--------------|-------------------|
| 8 | 21 | "$m^3/g;$" | -- $m^2/g;$ -- |
| 8 | 22 | "$cm^2/g;$" | -- $cm^3/g;$ -- |

Signed and Sealed this

Twenty-first Day of May, 1996

Attest:

BRUCE LEHMAN

*Attesting Officer*  *Commissioner of Patents and Trademarks*